United States Patent
Heesch et al.

(10) Patent No.: US 9,259,545 B2
(45) Date of Patent: Feb. 16, 2016

(54) PROCESS FOR CHECKING THE FUNCTION OF A RESPIRATION SYSTEM

(75) Inventors: Ralf Heesch, Lübeck (DE); Till Rahlf, Stockelsdorf (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 806 days.

(21) Appl. No.: 13/457,723

(22) Filed: Apr. 27, 2012

(65) Prior Publication Data

US 2013/0112204 A1    May 9, 2013

(30) Foreign Application Priority Data

Nov. 5, 2011    (DE) .......................... 10 2011 117 786

(51) Int. Cl.
| | |
|---|---|
| *A61M 16/00* | (2006.01) |
| *A62B 7/00* | (2006.01) |
| *F16K 31/02* | (2006.01) |
| *A61M 16/08* | (2006.01) |
| *A61M 16/20* | (2006.01) |
| *A61M 16/22* | (2006.01) |

(52) U.S. Cl.
CPC ............ *A61M 16/00* (2013.01); *A61M 16/0891* (2014.02); *A61M 16/201* (2014.02); *A61M 16/0078* (2013.01); *A61M 16/208* (2013.01); *A61M 16/22* (2013.01); *A61M 2016/0027* (2013.01); *A61M 2205/702* (2013.01)

(58) Field of Classification Search
CPC ............ A61M 16/00; A61M 16/0003; A61M 2016/0039; A61M 2016/0021; A61M 16/20; A61M 2016/0027; A61M 2016/0042; A61M 16/08; A61M 16/209; A61M 16/0018
See application file for complete search history.

(56) References Cited

U.S. PATENT DOCUMENTS

| | | | | |
|---|---|---|---|---|
| 5,129,390 | A | * | 7/1992 | Chopin et al. ............ 128/204.21 |
| 5,490,499 | A | * | 2/1996 | Heinonen et al. ......... 128/203.28 |
| 5,730,323 | A | * | 3/1998 | Osborne .......................... 222/55 |
| 5,810,002 | A | | 9/1998 | Dittmann |
| 6,024,089 | A | * | 2/2000 | Wallace et al. ........... 128/204.21 |
| 6,095,137 | A | | 8/2000 | Wallroth et al. |
| 2005/0133033 | A1 | | 6/2005 | Kruger et al. |
| 2006/0207593 | A1 | * | 9/2006 | Dittmann et al. ......... 128/203.12 |
| 2006/0260612 | A1 | * | 11/2006 | Matthiessen .............. A62B 7/04 128/205.13 |
| 2008/0053441 | A1 | * | 3/2008 | Gottlib et al. ............. 128/204.23 |
| 2008/0264417 | A1 | * | 10/2008 | Manigel et al. ........... 128/204.21 |
| 2009/0277448 | A1 | * | 11/2009 | Ahlmen ............. A61M 16/0051 128/204.21 |
| 2011/0061650 | A1 | * | 3/2011 | Heesch ..................... 128/203.12 |

FOREIGN PATENT DOCUMENTS

| | | |
|---|---|---|
| DE | 10 2004 011 907 A1 | 10/2005 |
| EP | 0 621 049 A1 | 10/1994 |

* cited by examiner

*Primary Examiner* — Jason Flick
*Assistant Examiner* — Eric Bryant
(74) *Attorney, Agent, or Firm* — McGlew and Tuttle, P.C.

(57) ABSTRACT

The function of a respiration system, with a patient port (1) with connected inspiration branch (3) and expiration branch, is checked. A rebreathing line (9) connects the inspiration branch to the expiration branch. A reservoir (25) is connected to a reservoir port (27) in the rebreathing line. An actuatable control valve (29) is provided in the rebreathing line between the expiration branch and the reservoir port. A pressure sensor (33) is connected to the rebreathing line. A control unit (39) is connected to the control valve and to pressure sensor. The process includes closing the control valve for a preset inspiration time and opening it for a preset expiration time. The value sent by the pressure sensor is detected with the control valve opened during the expiration time and compared with a preset first threshold valve. An error message is generated when the value sent exceeds the first threshold value.

20 Claims, 1 Drawing Sheet

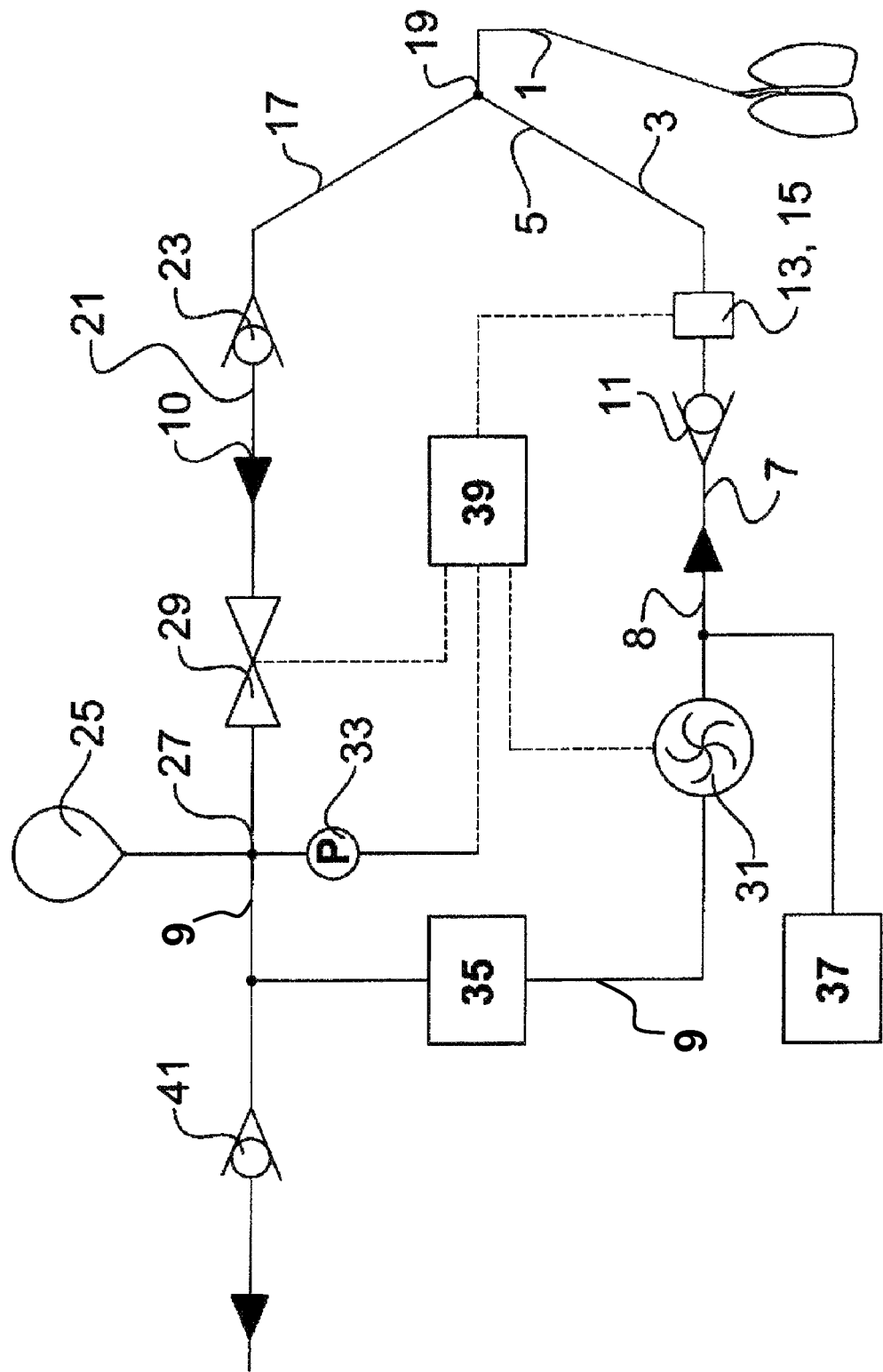

PROCESS FOR CHECKING THE FUNCTION OF A RESPIRATION SYSTEM

CROSS REFERENCE TO RELATED APPLICATIONS

This application claims the benefit of priority under 35 U.S.C. §119 of German Patent Application DE 10 2011 117 786.1 filed Nov. 5, 2011, the entire contents of which are incorporated herein by reference

FIELD OF THE INVENTION

The present invention pertains to a process for checking the function of a respiration system (also known as ventilation system) with a rebreathing line and a reservoir.

BACKGROUND OF THE INVENTION

Such a respiration system is known through the instructions for use for the "Zeus Infinity Empowered" system of Dräger Medical GmbH. Such respiration systems with a rebreathing line are designed, as a rule, such that based on a patient port or Y-piece, via which a patient is connected to the respiration system, an inspiration branch and an expiration branch are provided, whose ends located away from the patient port are connected to one another via the rebreathing line, which extends in the housing of the respiration system. A reservoir, such as a manual breathing bag for receiving breathing gas, a $CO_2$ absorber and a respiration drive, preferably in the form of a radial compressor, with which breathing gas can be delivered into the inspiration branch, are provided, as a rule, in the rebreathing line.

In addition, nonreturn valves, which prevent breathing gas expired by the patient from leaving the inspiration branch and breathing from being able to be pressed from the rebreathing line directly in the expiration branch, are provided in the respective inspiration and expiration branches. Finally, a control valve or positive end-expiratory pressure (PEEP) valve, which can be opened or closed by a control, is arranged close to the connection between the expiration branch and the rebreathing line.

The control valve is closed during the inspiration phase in order to prevent breathing gas from being pressed directly again into the rebreathing line by the respiration drive instead of being pressed into the patient port. However, the control valve is opened during the expiration phase, so that the breathing gas discharged from the patient port can flow back from the expiration branch into the rebreathing line, and this breathing gas first enters the reservoir, i.e., usually the manual breathing bag.

Breathing gas is thus drawn during normal respiration operation at first during the inspiration phase by means of the respiration drive from the reservoir and returned to the patient port via the inspiration branch, and the control valve is closed during this phase. The control valve is opened during the expiration phase, and the expired gas returns again into the reservoir.

However, the problem may arise now that the reservoir or the manual breathing bag has too small a volume. Part of the gas arriving from the patient port is discharged now via a gaseous anesthetic escape valve (hereinafter called "NGF valve") provided in the rebreathing line. However, the consequence of this is that an insufficient quantity of gas will be present in the system for the next inspiration phase and this gas must be compensated by feeding fresh gases. The respiration system cannot now be operated in the manner actually intended, in which latter case only a very small quantity of expensive gases must be fed anew.

SUMMARY OF THE INVENTION

Based on the state of the art, an object of the present invention is therefore to provide a process for a respiration system described in the introduction, with which an excessively small volume of the reservoir in the rebreathing line is reliably recognized.

This object is accomplished according to the present invention by a process for checking the function of a respirator with a patient port, an inspiration branch, which has a first end and a second end, as well as a nonreturn valve, which opens when the pressure on the side of the nonreturn valve facing the second end is above that on the side of the nonreturn valve facing the first end, wherein the first end is connected to a patient port, with an expiration branch, which has a first end and a second end, as well as a nonreturn valve, which opens when the pressure on the side of the nonreturn valve facing the first end is above that on the side of the nonreturn valve facing the second end, wherein the first end is connected to the patient port, with a rebreathing line, which connects the second end of the inspiration branch to the second end of the expiration branch, with a reservoir, which has a variable volume with a maximum volume, and which is connected to a reservoir port in the rebreathing line, with an actuatable control valve, which is provided in the rebreathing line between the second end of the expiration branch and the reservoir port, with a pressure sensor, which is connected to the rebreathing line adjacent to the reservoir port, and with a control unit, which is connected to the actuatable control valve and to the pressure sensor. The process comprises the following steps:
  Closing of the actuatable control valve for a preset inspiration time and
  Opening of the actuatable control valve for a preset expiration time, wherein
with the control valve opened during the expiration time, the value sent by the pressure sensor is detected and compared with a preset first threshold value, and wherein
  a first error message is generated when the value sent exceeds the first threshold value.

The pressure can be measured close to the reservoir by means of the pressure sensor, which is preferably provided directly at the reservoir port. When the reservoir or the manual breathing bag has a maximum volume that is too small, an overpressure, which is detected by the pressure sensor, is generated at first during the expiration phase at the end of an expiration stroke in this area. When this overpressure is above a preset threshold, an error message is sent for a user, and it is clear based on the overpressure that the maximum volume of the reservoir or manual breathing bag is not sufficient.

This process can also be carried out when the respiration system has no respiration drive or this drive is switched off. However, it is preferred for the process to be carried out with support of a respiration drive. It is, furthermore, preferred to design the respiration drive as a radial compressor.

Furthermore, the duration of the time period elapsing after the beginning of the expiration time until the value sent by the pressure sensor exceeds a first threshold value can be measured in a preferred embodiment. The shorter this duration, the larger is the volume missing in the reservoir, so that it is possible to adapt the error message to the degree by which the maximum volume of the manual breathing bag or reservoir is too small.

In addition, it is preferred if the value sent by the pressure sensor is also detected with the control valve closed during the inspiration time and compared with a preset second threshold value, in which case an error message is generated when the value sent drops below the second threshold value. The fact that a negative pressure becomes established at the pressure sensor in case of an undersized reservoir during the inspiration phase when the total amount of gas has been removed from the reservoir by the respiration drive and already fed to the patient port through the inspiration branch is utilized in this mode of operation. The appearance of a negative pressure below a preset threshold value during the inspiration phase is thus likewise an indicator of a manual breathing bag being selected to be too small.

The duration of the time period elapsing after the beginning of the inspiration phase until the value sent by the pressure sensor drops below the second threshold value can likewise be measured in this connection in another preferred embodiment. This duration is likewise an indicator of the degree by which the reservoir is undersized.

In another preferred embodiment, the respiration system has a fresh gas supply, with which at least gas components absorbed during the inspiration phase can be compensated.

Finally, it is also preferred if a volume flow sensor and a pressure sensor are provided in the inspiration branch, so that the inspiration phase and the expiration phase can be monitored by the control unit.

The present invention will be explained in more detail below on the basis of a drawing showing only a preferred exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which the preferred embodiment of the invention is illustrated.

BRIEF DESCRIPTION OF THE DRAWING

FIG. 1 is a schematic view showing a gas path of a respiration system for carrying out an exemplary embodiment of the process according to the present invention.

DESCRIPTION OF THE PREFERRED EMBODIMENT

Referring to the drawings in particular, the respiration system shown in FIG. 1 has, at first, a patient port 1, via which a patient can be connected to the respiration system. Patient port 1 is designed as a Y-piece, from which extends an inspiration branch 3, which has a first end 5, which is connected to the patient port 1, and a second end 7, with which the inspiration branch 3 is connected to an outlet 8 of a rebreathing line 9, which is provided in the housing of the respiration system and which also has, besides, an inlet 10.

Finally, a nonreturn valve 11 is also provided in the inspiration branch, this nonreturn valve being designed such that it opens only when the pressure on the side of the nonreturn valve 11, which side faces the second end 7, is higher than on the side that faces the first end 5. It is thus ensured that breathing gas cannot flow from the first end 5 to the second end 7 of inspiration branch 3.

In addition, a volume flow sensor 13 and a pressure sensor 15 are also arranged in the inspiration branch 3 in the preferred exemplary embodiment being shown here in order to make it possible to detect the corresponding parameters of the breathing gas flow that appear there.

The respiration system has, furthermore, an expiration branch 17, whose first end 19 is connected to the patient port 1 and whose second end 21 is connected to inlet 10 of rebreathing line 9. In addition, a nonreturn valve 23 is likewise provided in expiration branch 17, but this nonreturn valve 23 is designed such that it opens only when the pressure on the side of the nonreturn valve 23, which faces the first end 19, is higher than the pressure on the side that faces the second end 21. As a result, the expiration branch is designed such that breathing gas can flow in it only away from patient port 1 to inlet 10 of rebreathing line 9 but not the other way around.

As is also apparent from FIG. 1, a reservoir 25, which is designed as a manual breathing bag in this preferred embodiment and is connected to rebreathing line 9 via a reservoir port 27, is provided in rebreathing line 9. Reservoir 25 has a variable volume with a maximum volume, wherein the volume can be increased to the maximum volume on admission of pressure without any appreciable resistance. An actuatable control valve 29 (PEEP valve), which can be opened or closed electronically, is provided in rebreathing line 9 between reservoir port 27 and inlet 10 of rebreathing line 9. In addition, rebreathing line 9 has a respiration drive 31 between reservoir port 27 and outlet 8, said respiration drive preferably being a radial compressor and being able to be used to generate a flow in rebreathing line 9 from inlet 10 to outlet 8. Finally, a pressure sensor 33, with which the pressure in the rebreathing line can be measured in the area of reservoir port 27, is also connected to reservoir port 27.

As can also be recognized from FIG. 1, a $CO_2$ absorber 35, with which CO2 released by the patient can be absorbed, is also arranged in rebreathing line 9. Furthermore, a fresh gas supply 37 is provided, with which fresh gas can be fed into rebreathing line 9. this taking place downstream of respiration drive 31.

To control the components of the respiration system, a control unit 39 is, finally, provided, which is connected to the volume sensor flow 13, pressure sensor 15, control valve 29, pressure sensor 33 and respiration drive 31.

To enable excess gas to be discharged from rebreathing line 9, a gaseous anesthetic escape valve ("NGF valve") 41 is provided, which opens at a preset threshold.

The above-described respiration system operates according to the process according to the present invention as follows.

After an expiration phase, during which reservoir 25 in the form of a manual breathing bag has been filled, actuatable control valve 29 is closed by control unit 39, and respiration drive 31 is operated in this preferred exemplary embodiment during the subsequent inspiration time in order to generate a flow in rebreathing line 9 from reservoir 25 to the second end 7 of inspiration branch 3, so that breathing gas is drawn through the $CO_2$ absorber 35 from reservoir 25 and fed to patient port 1.

The value sent by pressure sensor 33 during the inspiration time is detected by control unit 39 and compared with a preset second threshold value. If the value sent drops below the second threshold value, an error message is sent. In addition, the duration of the time period elapsing between the closing of actuatable control valve 29 and the point in time at which the value sent by pressure sensor 33 drops below the second threshold value is measured.

The second threshold value is selected to be such that a value dropping below this value means that a vacuum, which can be attributed to the fact that reservoir 25 has been completely emptied, even though the inspiration time has not yet been reached, has developed in the area of reservoir port 27. The error message varies depending on the measured duration of the time period between the beginning of the inspiration time and the point in time at which the value drops below the second threshold value, a short time period indicating that the volume of reservoir 25 is much too small, while a comparatively long time period, which is only slightly shorter than the duration of the inspiration phase, indicates that the volume of reservoir 25 is too small only slightly. The error message is adapted correspondingly.

Actuatable control valve 29 is subsequently opened, and respiration drive 31 is operated at reduced capacity in the preferred exemplary embodiment being described here, so that nonreturn valve 11 in inspiration branch 3 remains closed. Breathing gas flows during the expiration time through expiration branch 17, control valve 29 and reservoir port 27 into reservoir 25, which is now being filled continuously. The pressure at reservoir port 27 is again detected by means of pressure sensor 33, the value sent by pressure sensor 33 is compared in control unit 39 with a first threshold value, and an error message is sent when the value sent exceeds the first threshold value.

The first threshold value is selected to be such that exceeding this value means that an overpressure, which comes into being due to the fact that reservoir 25 is filled completely and can be filled further only by overcoming a resistance, which is brought about, for example, by the elasticity of the manual breathing bag, develops in the area of reservoir port 27. When this happens, the additional breathing gas arriving from the patient port is released via NGF valve 41.

However, when there is no build-up of pressure, which would exceed the first threshold value, in the area of reservoir port 27, this indicates that the volume of reservoir 25 is large enough and no error message is sent.

The duration of the time period that is between the beginning of the expiration time, i.e., the closing of control valve 29, and the exceeding of the first threshold value by the value sent by pressure sensor 33 is also measured during the expiration time. The shorter this duration, the greater is the degree by which the maximum volume of reservoir 25 is undersized, and the error message sent is adapted depending on this duration.

The above-described exemplary embodiment is provided with a respiration drive 31. However, the process according to the present invention may also be carried out without such a respiration drive by switching the controllable valve 29. It is advantageous in this case if volume sensor 13 and pressure sensor 15 are present in inspiration branch 3, so that the corresponding parameters can be detected by control unit 39.

To check whether the volume of reservoir 25 is sufficient, it is only necessary to detect the pressure in the area of reservoir port 27 during the expiration phase to make it possible to measure a pressure being built up there, which indicates that the capacity of reservoir 25 is too small, so that an error message can then be sent, on the basis of which the human operator may possibly use another reservoir, which has the necessary capacity.

Using the process according to the present invention, it is consequently possible to determine in a simple manner that a respiration system is dimensioned incorrectly. Measurement of the duration of the time period between the beginning of the inspiration or expiration phase and the point in time at which the respective threshold value is exceeded or undershot makes it possible to determine the extent by which the volume of reservoir 25 is too small.

While a specific embodiment of the invention has been shown and described in detail to illustrate the application of the principles of the invention, it will be understood that the invention may be embodied otherwise without departing from such principles.

APPENDIX

List of Reference Numbers

1 Patient port, Y-piece
3 Inspiration branch
5 First end (inspiration branch)
7 Second end (inspiration branch)
8 Outlet of rebreathing line
9 Rebreathing line
10 Inlet of rebreathing line
11 Nonreturn valve (inspiration branch)
13 Volume flow sensor (inspiration branch)
15 Pressure sensor (inspiration branch)
17 Expiration branch
19 First end (expiration branch)
21 Second end (expiration branch)
23 Nonreturn valve (expiration branch)
25 Reservoir (manual breathing bag)
27 Reservoir port
29 Control valve
31 Respiration drive (radial compressor)
33 Pressure sensor (reservoir)
35 $CO_2$ absorber
37 Fresh gas supply
39 Control unit 39
41 Gaseous anesthetic escape valve (NGF valve)

What is claimed is:

1. A process for checking a function of a respiration system comprising a patient port, an inspiration branch, which has an inspiration branch first end and an inspiration branch second end as well as an inspiration branch nonreturn valve, which opens when pressure on a side of the inspiration branch nonreturn valve facing the inspiration branch second end is above pressure on a side of the inspiration branch nonreturn valve facing the inspiration branch first end, wherein the inspiration branch first end is connected to the patient port, with an expiration branch, which has an expiration branch first end and an expiration branch second end as well as an expiration branch nonreturn valve, which opens when pressure on a side of the expiration branch nonreturn valve facing the expiration branch first end is above pressure on the side of the expiration branch nonreturn valve facing the expiration branch second end, wherein the expiration branch second end is connected to the patient port, with a rebreathing line, which connects the inspiration branch second end to the expiration branch second end, with a reservoir, which has a variable volume with a maximum volume and which is connected to a reservoir port in the rebreathing line, with an actuatable control valve, which is provided in the rebreathing line between the expiration branch second end and the reservoir port, with a pressure sensor, which is connected to the rebreathing line adjacent to the reservoir port, and with a control unit, which is connected to the actuatable control valve and to the pressure sensor, the process comprising the steps of:

closing the actuatable control valve for a preset inspiration time;

opening the actuatable control valve for a preset expiration time;

providing a value as output via the pressure sensor, which is connected to the rebreathing line adjacent to the reservoir port;

detecting said value sent by the pressure sensor, with the actuatable control valve opened during an expiration phase;

comparing the value detected with a preset threshold value; and generating an error message when the value detected exceeds the preset threshold value.

2. A process in accordance with claim 1, wherein:

the respiration system has a respiration drive, which is arranged in the rebreathing line between the reservoir port and the inspiration branch second end;

the respiration drive is operated during an inspiration time to generate a flow in the rebreathing line from the reservoir to the inspiration branch second end; and the respiration drive is switched off during an expiration time or is operated at reduced capacity, so that the nonreturn valve in inspiration branch remains closed.

3. A process in accordance with claim 1, further comprising:

measuring a duration of a time period between the opening of the control valve and a point in time at which the value sent by pressure sensor exceeds the preset threshold value; and varying the error message depending on the measured duration.

4. A process in accordance with claim 1, further comprising:

detecting a value sent by the pressure sensor, with the actuatable control valve closed during an inspiration time;

comparing the value detected, with the actuatable control valve closed, with another preset threshold value; and generating an error message when the value detected, with the actuatable control valve closed, drops below the another preset threshold value.

5. A process in accordance with claim 4, further comprising:

measuring a duration of a time period between a closing of control valve and a point in time at which the value sent by pressure sensor drops below the another threshold value; and varying the another error message depending on the measured duration.

6. A process in accordance with claim 1, wherein the reservoir comprises a manual breathing bag.

7. A process in accordance with claim 1, wherein the respiration system has a fresh gas supply, which is connected to the rebreathing line and with which fresh gas is fed into rebreathing line.

8. A process in accordance with claim 1, further comprising:

providing a volume flow sensor and a pressure sensor in the inspiration branch; and detecting the pressure and a volume flow during an inspiration time and an expiration time.

9. A process in accordance with claim 1, wherein the pressure sensor is arranged at the reservoir port.

10. A process for checking a function of a respiration system, the process comprising the steps of:

providing the respiration system with a patient port, an inspiration branch, which has an inspiration branch first end and an inspiration branch second end as well as an inspiration branch nonreturn valve, which opens when a pressure on a side of the inspiration branch nonreturn valve facing the inspiration branch second end is above a pressure on a side of the inspiration branch nonreturn valve facing the inspiration branch first end, wherein the inspiration branch first end is connected to the patient port, with an expiration branch, which has an expiration branch first end and an expiration branch second end as well as an expiration branch nonreturn valve, which opens when a pressure on a side of the expiration branch nonreturn valve facing the expiration branch first end is above a pressure on the side of the expiration branch nonreturn valve facing the expiration branch second end, wherein the expiration branch second end is connected to the patient port, with a rebreathing line, which connects the inspiration branch second end to the expiration branch second end, with a reservoir, which has a variable volume with a maximum volume and which is connected to a reservoir port in the rebreathing line, with an actuatable control valve, which is provided in the rebreathing line between the expiration branch second end and the reservoir port, with a pressure sensor, which is connected to the rebreathing line adjacent to the reservoir port, and with a control unit, which is connected to the actuatable control valve and to the pressure sensor;

closing the actuatable control valve for a preset inspiration time;

opening the actuatable control valve for a preset expiration time; and at least one of:

detecting a value sent by the pressure sensor, with the actuatable control valve opened during an expiration phase, comparing the value detected with a preset threshold value and generating an error message when the value detected exceeds the preset threshold value; and detecting a value sent by the pressure sensor, with the actuatable control valve closed during the inspiration time, comparing the value detected, with the actuatable control valve closed, with another preset threshold value and generating an error message when the value detected, with the actuatable control valve closed, drops below the another preset threshold value.

11. A process in accordance with claim 10, wherein:

the respiration system has a respiration drive, which is arranged in the rebreathing line between the reservoir port and the inspiration branch second end;

the respiration drive is operated during an inspiration time to generate a flow in the rebreathing line from the reservoir to the inspiration branch second end; and the respiration drive is switched off during an expiration time or is operated at reduced capacity, so that nonreturn valve in inspiration branch remains closed.

12. A process in accordance with claim 11, further comprising at least one of:

measuring a duration of a time period between the opening of a control valve and a point in time at which the value sent by pressure sensor exceeds the preset threshold value and varying the error message depending on the measured duration; and measuring a duration of the time period between the closing of control valve and the point in time at which the value sent by pressure sensor drops below the another threshold value; and varying the another error message depending on the measured duration.

13. A process for checking a function of a respiration system comprising:

providing a patient port;

providing an expiration branch nonreturn valve;

providing an expiration branch comprising an expiration branch first end and an expiration branch second end, said expiration branch nonreturn valve opening when pressure on a side of the expiration branch nonreturn valve facing the expiration branch first end is above pressure on the side of the expiration branch nonreturn valve facing the expiration branch second end, wherein the expiration branch second end is connected to the patient port;

providing an inspiration branch nonreturn valve;

providing an inspiration branch, which has an inspiration branch first end and an inspiration branch second end, said inspiration branch nonreturn valve opening when pressure on a side of the inspiration branch nonreturn valve facing the inspiration branch second end is above a pressure on a side of the inspiration branch nonreturn valve facing the inspiration branch first end, wherein the inspiration branch first end is connected to the patient port;

providing a rebreathing line, which connects the inspiration branch second end to the expiration branch second end;

providing a reservoir, which has a variable volume with a maximum volume and which is connected to a reservoir port in the rebreathing line;

providing an actuatable control valve, which is provided in the rebreathing line between the expiration branch second end and the reservoir port;

providing a pressure sensor, which is connected to the rebreathing line adjacent to the reservoir port;

providing a control unit, which is connected to the actuatable control valve and to the pressure sensor;

closing the actuatable control valve for a preset inspiration time;

opening the actuatable control valve for a preset expiration time;

detecting said value sent by the pressure sensor, with the actuatable control valve opened during an expiration phase;

comparing the value detected with a preset threshold value; and generating an error message when the value detected exceeds the preset threshold value.

14. A process in accordance with claim 13, wherein:

the respiration system has a respiration drive, which is arranged in the rebreathing line between the reservoir port and the inspiration branch second end;

the respiration drive is operated during an inspiration time to generate a flow in the rebreathing line from the reservoir to the inspiration branch second end; and the respiration drive is switched off during an expiration time or is operated at reduced capacity, so that the nonreturn valve in inspiration branch remains closed.

15. A process in accordance with claim 13, further comprising:

measuring a duration of a time period between the opening of the control valve and a point in time at which the value sent by pressure sensor exceeds the preset threshold value; and varying the error message depending on the measured duration.

16. A process in accordance with claim 13, further comprising:

detecting a value sent by the pressure sensor, with the actuatable control valve closed during an inspiration time;

comparing the value detected, with the actuatable control valve closed, with another preset threshold value; and generating an error message when the value detected, with the actuatable control valve closed, drops below the another preset threshold value.

17. A process in accordance with claim 16, further comprising:

measuring a duration of a time period between a closing of control valve and a point in time at which the value sent by pressure sensor drops below the another threshold value; and varying the another error message depending on the measured duration.

18. A process in accordance with claim 13, wherein the reservoir comprises a manual breathing bag.

19. A process in accordance with claim 13, wherein the respiration system has a fresh gas supply, which is connected to the rebreathing line and with which fresh gas is fed into rebreathing line.

20. A process in accordance with claim 13, further comprising:

providing a volume flow sensor and a pressure sensor in the inspiration branch; and detecting the pressure and a volume flow during an inspiration time and an expiration time, wherein the pressure sensor is arranged at the reservoir port.

* * * * *

UNITED STATES PATENT AND TRADEMARK OFFICE
CERTIFICATE OF CORRECTION

PATENT NO. : 9,259,545 B2  
APPLICATION NO. : 13/457723  
DATED : February 16, 2016  
INVENTOR(S) : Heesch Page 1 of 1

It is certified that error appears in the above-identified patent and that said Letters Patent is hereby corrected as shown below:

Title Page, Item (30) Foreign Application Priority Data should read
-- Jul. 2, 2011   (DE)................................ 10 2011 106 413.7 --

In the Specification

Column 1, lines 8-9, "DE 10 2011 117 786.1 filed Nov. 5, 2011" should read -- DE 10 2011 106 413.7 filed Jul. 2, 2011 --

Signed and Sealed this  
Thirty-first Day of May, 2016

Michelle K. Lee  
*Director of the United States Patent and Trademark Office*